United States Patent [19]

Moore et al.

[11] 4,156,730
[45] May 29, 1979

[54] PHARMACEUTICALLY ACTIVE COMPOUNDS, PREPARATION THEREOF, INTERMEDIATES USEFUL IN SUCH PREPARATION AND COMPOSITIONS CONTAINING THE COMPOUNDS

[75] Inventors: Richard W. Moore; Frederick Cassidy, both of Harlow; Gordon Wootton, Sawbridgeworth, all of England

[73] Assignee: Beecham Group Limited, United Kingdom

[21] Appl. No.: 796,701

[22] Filed: May 13, 1977

[30] Foreign Application Priority Data

May 22, 1976 [GB] United Kingdom .............. 21304/76
Feb. 3, 1977 [GB] United Kingdom ................ 4380/77

[51] Int. Cl.² ................. C07D 207/32; A61K 31/40; C07D 207/20
[52] U.S. Cl. .................... 424/274; 546/205; 546/206; 546/220; 546/243; 260/326.33; 260/326.44; 424/267
[58] Field of Search .............. 260/326.45, 326.33; 424/274

[56] References Cited

U.S. PATENT DOCUMENTS

| 3,975,399 | 8/1976 | De Franco et al. ............. 260/326.2 |
| 4,003,911 | 1/1977 | Scribner ......................... 260/326.47 |

*Primary Examiner*—Donald G. Daus
*Assistant Examiner*—Mary C. Lee
*Attorney, Agent, or Firm*—Jacobs & Jacobs

[57] ABSTRACT

A compound of formula (I):

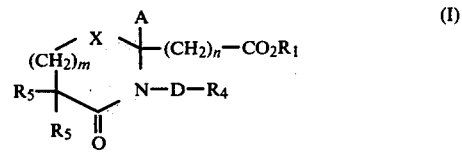

wherein:
m is 0 or 1;
n is 4 to 8;
A is hydrogen, and when m is 0 and $R_5$ is methyl it may also be methyl or a group $CO_2B$ wherein B is hydrogen or $CO_2B$ represents an ester group in which the B moiety contains from 1 to 12 carbon atoms;
X is CO, protected CO, CROH in which R is hydrogen or $C_{1-4}$ alkyl and in which the OH moiety may be protected; $R_1$ is hydrogen, or $CO_2R_1$ represents an ester group in which the $R_1$ moiety contains 1 to 12 carbon atoms;
$R_4$ is hydrogen, $C_{1-9}$ alkyl, $C_{5-8}$ cycloalkyl, $C_{5-8}$ cycloalkyl-$C_{1-6}$ alkyl, phenyl, phenyl $C_{1-6}$ alkyl, naphthyl, naphthyl $C_{1-6}$ alkyl, any of which phenyl or naphthyl moieties may be substituted by one or more halogen, trifluoromethyl, $C_{1-6}$ alkyl, $C_{1-6}$ alkoxy, or nitro groups;

D is a group
$-CH_2-CH(R_6)-CH(R_7)-C(R_2)(R_3)-$, a group $-CH_2-CH(R_6)-CH(R_7)-CH(R_8)-C(R_2)(R_3)-$, a group $-CH_2-CH(R_6)-CH(R_7)-CH(R_8)-CH(R_8^1)-C(R_2)(R_3)-$ or a group $-CH_2-C(R_{10})(R_3)-$ wherein $R_2$ is hydrogen, $C_{1-4}$ alkyl or phenyl;
$R_3$ is hydroxy or protected hydroxy; $R_6$, $R_7$, $R_8$ and $R_8^1$ are hydrogen, $C_{1-4}$ alkyl or phenyl; and $R_{10}$ is hydrogen, $C_{1-4}$ alkyl or phenyl; and
$R_5$ is hydrogen, and when m is 0 it may also be methyl; and salts thereof; have a range of pharmacological activities similar to those shown by the natural prostaglandins, but these activities tend to be rather more selective.

37 Claims, No Drawings

PHARMACEUTICALLY ACTIVE COMPOUNDS, PREPARATION THEREOF, INTERMEDIATES USEFUL IN SUCH PREPARATION AND COMPOSITIONS CONTAINING THE COMPOUNDS

This invention relates to novel compounds having pharmacological activity, to a process for their preparation, to intermediates useful in that process, and to pharmaceutical compositions containing them.

More specifically the invention relates to cyclic amides in which the nitrogen atom is substituted by an aliphatic or aliphatic-aromatic group and one α-carbon atom is substituted by an aliphatic group.

Natural prostaglandins and analogues thereof are known to possess a wide variety of pharmacological activities.

Offenlegungsschrift No. 2323193 discloses that pyrazolidine derivatives of the formula (I)':

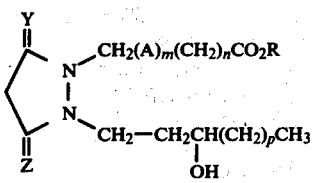

wherein A is CH=CH or C≡C; R is H, an alkali metal, an amine salt, or an ≯12C hydrocarbon or chlorohydrocarbon residue; m is 0 or 1; n is 0-6; p is 0-6; and Y and Z are O or $H_2$ except that Y and Z are not both O; have similar biological properties to the prostaglandins or are antagonists of prostaglandins.

Japanese Patent Application No. 51001461 discloses the preparation of a compound of formula (II)':

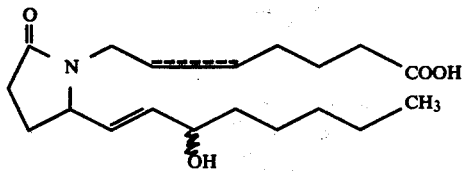

and states that this compound has laxative activity.

A novel class of compounds having useful pharmacological activity has now been discovered, which compounds are structurally distinct from the known compounds referred to above.

The present invention provides a compound of the formula (I):

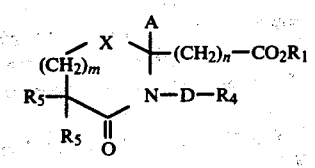

wherein:
m is 0 or 1;
n is 4 to 8;
A is hydrogen, and when m is 0 and $R_5$ is methyl it may also be methyl or a group $CO_2B$ wherein B is hydrogen or $CO_2B$ represents an ester group in which the B moiety contains from 1 to 12 carbon atoms;

X is CO, protected CO, CROH in which R is hydrogen or $C_{1-4}$ alkyl and in which the OH moiety may be protected;
$R_1$ is hydrogen, or $CO_2R_1$ represents an ester group in which the $R_1$ moiety contains 1 to 12 carbon atoms;
$R_4$ is hydrogen, $C_{1-9}$ alkyl, $C_{5-8}$ cycloalkyl, $C_{5-8}$ cycloalkyl-$C_{1-6}$ alkyl, phenyl, phenyl-$C_{1-6}$ alkyl, naphthyl, naphthyl-$C_{1-6}$ alkyl, any of which phenyl or naphthyl moieties may be substituted by one or more halogen, trifluoromethyl, $C_{1-6}$ alkyl, $C_{1-6}$ alkoxy, or nitro groups;
D is a group $-CH_2-CH(R_6)-CH(R_7)-C(R_2)(R_3)-$, a group $-CH_2-CH(R_6)-CH(R_7)-CH(R_8)-C(R_2)(R_3)-$, a group $-CH_2-CH(R_6)-CH(R_7)-CH(R_8)-CH(R_8^1)-C(R_2)(R_3)-$ or a group $-CH_2-C(R_{10})(R_3)-$ wherein $R_2$ is hydrogen, $C_{1-4}$ alkyl or phenyl;
$R_3$ is hydroxy or protected hydroxy; $R_6$, $R_7$, $R_8$ and $R_8^1$ are hydrogen, $C_{1-4}$ alkyl or phenyl; and $R_{10}$ is hydrogen, $C_{1-4}$ alkyl or phenyl; and
$R_5$ is hydrogen, and when m is 0 it may also be methyl; and salts thereof.

It is normally preferred that m is 0.
Suitably n is 5, 6 or 7, preferably 6.
A must be hydrogen when m is 1, and also when $R_5$ is hydrogen. When m is 0 and $R_5$ is methyl, A can be hydrogen, methyl or a group $CO_2B$ as defined. Suitable examples of B include hydrogen and methyl, ethyl, propyl, butyl, phenyl, benzyl, toluyl and the like, while normally for B hydrogen or $C_{1-4}$ alkyl are preferred. While the groups B and $R_1$ may be different, it is normally preferred that they are both hydrogen or the same $C_{1-4}$ alkyl group.

Suitable protected hydroxyl groups CROH and $R_3$ include readily hydrolysable groups such as acylated hydroxy groups in which the acyl moiety contains 1 to 4 carbon atoms, for example the acetoxy group; and hydroxy groups etherified by readily removable inert groups such as the benzyl or like groups. Preferably $R_3$ is hydroxy, and the hydroxy moiety in CROH is unprotected.

Suitable protected CO groups X include groups formed by conventional carbonyl addition and condensation reactions such as ketals, thioketals, hemithioketals, oximes, semicarbazones, hydrazones and the like. Of such groups often the ketal type derivatives will be most useful, for example when X is a group

Examples of suitable groups X include CO, CHOH, $C(CH_3)OH$ and $C(C_2H_5)OH$. Preferably X is CO, CHOH or $C(CH_3)OH$, most preferably CO.

$R_1$ is hydrogen or $CO_2R_1$ represents an ester group in which the $R_1$ moiety contains from 1 to 12 carbon atoms. Examples of $R_1$ include hydrogen, methyl, ethyl, propyl, butyl, phenyl, benzyl, toluyl and the like, while normally hydrogen or $C_{1-4}$ alkyl groups are preferred.

Of the groups possible for $R_2$, we have found that hydrogen, methyl, ethyl and phenyl are the most suitable. Of these groups, preferred groups include methyl and ethyl.

Preferably $R_3$ is hydroxy.

Suitable groups $R_4$ when $R_4$ is an alkyl group include $C_{3-9}$ alkyl groups. Such $C_{3-9}$ alkyl groups may be straight chain alkyl groups, such as n-propyl, n-butyl, n-pentyl, n-hexyl, n-heptyl and n-octyl or may be alkyl groups branched by one or two methyl groups (at the same or different carbon atoms). Thus for example, $R_4$ may be a group $CH_2R_{11}$, $CH(CH_3)R_{11}$ or $C(CH_3)_2R_{11}$, wherein $R_{11}$ is a straight chain alkyl group such that the carbon content of the resultant group $R_4$ is 3 to 9. The $-D-R_4$ moiety in formula (I) when $R_4$ is an alkyl group will not normally exceed 12 carbons in length.

When $R_4$ is or contains a $C_{5-8}$ cycloalkyl moiety, the moiety is suitably a cyclohexyl moiety. Examples of suitable $C_{1-6}$ alkyl moieties when $R_4$ is a $C_{5-8}$ cycloalkyl-$C_{1-6}$ alkyl group include methyl, ethyl, propyl, butyl and amyl.

When $R_4$ is an aryl group as previously defined, suitable groups $R_4$ include phenyl, phenylmethyl, phenylethyl, phenyl n-propyl, phenyl n-butyl, naphthyl, naphthylmethyl, naphthylethyl, naphthyl n-propyl and naphthyl n-butyl. These groups may be substituted in the phenyl or naphthyl moiety by normally one, two or three groups selected from those substituent groups listed herein before. Examples of suitable substituent groups include fluorine, chlorine and bromine atoms and $CF_3$, methyl, ethyl, n- and iso-propyl, methoxy and ethoxy, n- and iso- propoxy and nitro groups.

When m is 1, $R_5$ must be hydrogen. However it may be hydrogen or methyl when m is 0, and often compounds wherein $R_5$ is methyl in this manner have particularly useful pharmacological properties and beneficial stability.

$R_6$, $R_7$, $R_8$ and $R_8^1$ are separately hydrogen, $C_{1-4}$ alkyl or phenyl. Suitable examples of such groups include hydrogen, methyl, ethyl and phenyl; preferred examples include hydrogen, methyl and ethyl.

$R_{10}$ is hydrogen, $C_{1-4}$ alkyl or phenyl. Suitable examples of such groups include hydrogen, methyl, ethyl and phenyl, preferably methyl and ethyl.

The compounds of the formula (I) may form conventional acid salts when $R_1$ is hydrogen. Such salts include those with alkali and alkaline earth metals, suitably sodium and potassium, and ammonium and substituted ammonium salts.

A particularly suitable class of compounds within formula (I) are those wherein D is a group $-CH_2-CH(R_6)-CH(R_7)-C(R_2)(R_3)-$, a group $-CH_2-CH(R_6)-CH(R_7)-CH(R_8)-C(R_2)(R_3)-$, or a group $-CH_2-C(R_{10})(R_3)-$.

It will of course be realised that the compounds of the formula (I) can have asymmetric centres, and thus are capable of existing in a number of stereoisomeric forms. The invention extends to each of these stereoisomeric forms, and to mixtures thereof. The different stereoisomeric forms may be separated one from the other by the usual methods.

From the aforesaid it may be seen that one particularly suitable sub-group of compounds within the formula (I) are those of the formula (II):

$$\underset{(CH_2)_m}{\overset{X}{\diagup}}\underset{N}{\diagdown}\underset{\overset{\|}{O}}{\diagup}\overset{(CH_2)_pCO_2R_1^1}{\underset{R_6}{\diagdown}}\underset{R_7}{\diagdown}\overset{R_2}{\underset{OH}{\diagup R_4^1}} \quad \text{(II)}$$

wherein:
m is 0 or 1;
p is 5, 6 or 7;
$X^1$ is CO, protected CO, CHOH or $C(CH_3)OH$;
$R_1^1$ is hydrogen or $C_{1-4}$ alkyl;
$R_2$, $R_6$ and $R_7$ are as defined in formula (I);
$R_4^1$ is $C_{3-8}$ alkyl, or a group of formula (III), (IV) or (V) as defined below:

$$-(CH_2)_q-\underset{Y}{\diagdown}\overset{W}{\diagup}\underset{Z}{\diagdown} \quad \text{(III)}$$

or:

$$-(CH_2)_q-\underset{Y}{\diagdown}\overset{W}{\diagup}\underset{Z}{\diagdown} \quad \text{(IV)}$$

$$-(CH_2)_q-\overset{(CH_2)_r}{\diagup}\diagdown \quad \text{(V)}$$

wherein:
q is 0 to 5;
r is 0 to 3; and
W, Y, Z are separately hydrogen, fluorine, chlorine, bromine, $CF_3$, methyl, ethyl, n- or iso-propyl, methoxy ethoxy, n- or iso-propoxy or nitro groups; and salts thereof.

In formula (II) it is generally preferred that m is 0.
p is most suitably 6.
$X^1$ is preferably CO or protected CO, most preferably CO.

$R_2$ is most suitably methyl, ethyl or phenyl, preferably methyl or ethyl.

$R_6$ and $R_7$ are suitably hydrogen, methyl or ethyl.

When $R_4^1$ is a $C_{3-8}$ alkyl group, suitable and preferred groups $R_4^1$ include those previously described as suitable and preferred alkyl groups for $R_4$. Examples of such groups include straight chain propyl, pentyl and hexyl, and of these normally the most useful is pentyl.

A particularly preferred sub-group of compounds within the formula (I) are those of the formula (VI):

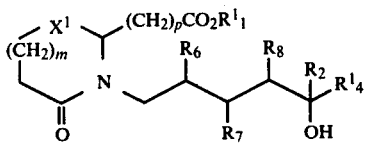

wherein the variables are as defined in formula (II), except for $R_8$ which is as defined in formula (I).

$R_8$ is suitably hydrogen, methyl or ethyl.

Suitable and preferred values for the other variables are as described for formula (II) compounds.

A further group of compounds within those of formula (I) are those of formula (VII):

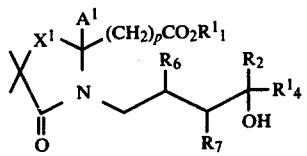

wherein the variables are as defined in formula (II), except for $A^1$ which is hydrogen, a group $CO_2R_1^1$, or methyl.

Preferably $A^1$ is hydrogen or methyl.

Suitable and preferred values for the other variables are as described for formula (II) compounds.

Another group of compounds within those of formula (I) are those of formula (VIII):

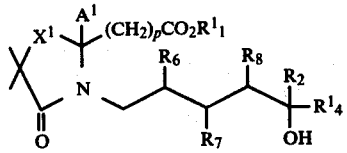

wherein the variables are as defined in formula (VI) and formula (VII).

Suitable and preferred values for these variables are as previously described for formula (VI) and formula (VII) compounds.

The aforesaid sub-groups (II), (VI), (VII) and (VIII) refer to compounds of the formula (I) wherein the side chain attached to nitrogen has a 4 or 5-hydroxy group (numbering from nitrogen). Important sub-groups within formula (I) also exist when this side chain has a 2-hydroxy group, and these sub-groups include the following:

Compounds of the formula (IX):

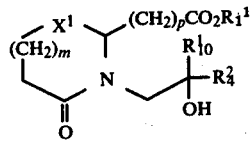

wherein:
 m, p, $X^1$ and $R_1^1$ are as defined in formula (II);
 $R_{10}^1$ is hydrogen, $C_{1-4}$ alkyl or phenyl; and
 $R_4^2$ is $C_{5-9}$ alkyl, or a group of formula (III), (IV) or (V) as hereinbefore defined;
and salts thereof.

In formula (IX), it is generally preferred that m is 0. p is most suitably 6. $X^1$ is preferably CO or protected CO, most preferably CO.

$R_{10}^1$ is suitably hydrogen, methyl or ethyl, preferably methyl.

When $R_4^2$ is a $C_{5-9}$ alkyl group, it is suitably a straight chain alkyl group such as n-pentyl, n-hexyl, n-heptyl and n-octyl, optionally branched by one or two methyl groups. Examples of such alkyl groups include —$CH_2R_{12}$, $CH(CH_3)R_{12}$ and $C(CH_3)_2R_{12}$ wherein $R_{12}$ is a straight chain alkyl group such that the carbon content of the resultant group $R_4^2$ is 5 to 9.

Compounds of the formula (X):

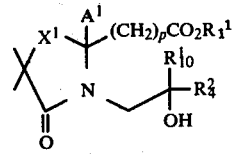

wherein: the variables are as defined in formula (IX) except for $A^1$ which is hydrogen, a group $CO_2R_1^1$, or methyl; and salts thereof.

Preferably $A^1$ is hydrogen or methyl.

Suitable and preferred values for the other variables are as described for formula (IX) compounds.

Important sub-groups within formula (I) also exist when the —D—$D_4$ side chain has a 6-hydroxy group (numbering from nitrogen), and these sub-groups include compounds of formula (A):

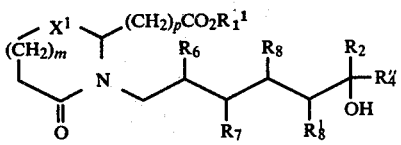

wherein:
 m is 0 or 1;
 p is 5, 6 or 7;
 $X^1$ is CO, protected CO, CHOH or $C(CH_3)OH$;
 $R_1^1$ is hydrogen or $C_{1-4}$ alkyl;
 $R_2$, $R_6$, $R_7$, $R_8$ and $R_8^1$ are as defined in formula (I);
 $R_4''$ is a $C_{1-6}$ alkyl group, or a group of formula (B), (C) or (D):

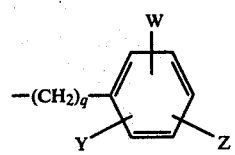

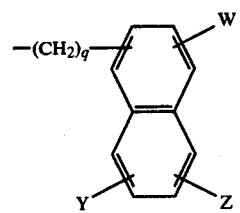

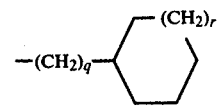

wherein: q is 0 to 5, r is 0 to 3 and W, Y and Z are separately hydrogen, fluorine, chlorine, bromine, $CF_3$, methyl, ethyl, n- or iso-propyl, methoxy, ethoxy, n- or iso-propoxy or nitro groups; and salts thereof.

In formula (A) it is generally preferred that m is 0.
p is most suitably 6.

$X^1$ is preferably CO or protected CO, most preferably CO.

$R_2$ is most suitably methyl, ethyl or phenyl, preferably methyl or ethyl.

$R_6$, $R_7$, $R_8$ and $R_8^1$ are suitably hydrogen, methyl or ethyl, preferably hydrogen.

When $R_4''$ is a $C_{1-6}$ alkyl group, it is suitably n-propyl or n-butyl.

Often in formulae (B) and (C) at least Y and Z will be hydrogen.

Preferably in formula (D) r is 1.

Other interesting sub-groups when the —D—$R_4$ side chain has a 6-hydroxy group include those compounds of formula (E):

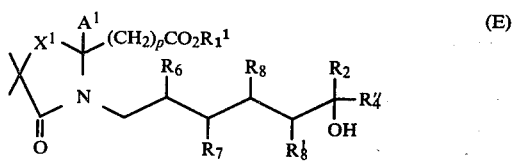

(E)

wherein the variable groups are as defined with respect to formula (A), except for $A^1$ which is hydrogen, a group $CO_2R_1^1$, or methyl; and salts thereof.

Preferably $A^1$ is hydrogen or methyl.

Suitable and preferred values for the other variables are as described for formula (A) compounds.

The invention also provides a number of processes for preparing the compounds of formula (I):

1. Compounds of formula (I) wherein m is 0, $R_5$ is methyl and A is hydrogen or $CO_2B$ The process comprises the methylation of a compound of formula (XI):

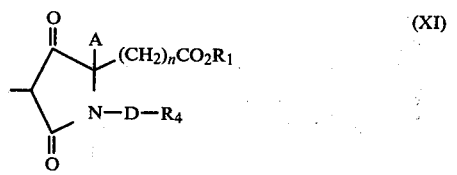

(XI)

wherein n, $R_1$, D and $R_4$ are as defined in formula (I), and A is hydrogen or $CO_2B$ to yield a compound of the formula (I) wherein X is CO; and thereafter if desired converting X in the thus formed compound to protected CO by conventional methods, or to CROH by reduction when R is hydrogen or by reaction with a $C_{1-4}$ alkyl Grignard reagent or $C_{1-4}$ alkyl metallic complex when R is $C_{1-4}$ alkyl, and then optionally protecting the CROH hydroxy moiety.

The methylation is conveniently carried out by reacting the chosen compound of the formula (XI) with a strong base and a source of $CH_3^\oplus$ ions in an inert solvent. Suitable strong bases include sodium hydride, suitable sources of $CH_3^\oplus$ ions include the methyl halides such as methyl iodide, and suitable inert solvents include benzene and the like.

2. Compounds of the formula (I) wherein m is 0, $R_5$ is methyl and A is methyl.

The process comprises methylating a compound of the formula (I) wherein m is 0, $R_5$ is methyl, A is hydrogen and X is CO; and thereafter if desired carrying out the optional X conversions described in process 1.

The methylation is suitably carried out as for a compound of formula (XI) in 1., but in a more polar solvent such as dimethylformamide.

3. Compounds of the formula (I) wherein m is 0, $R_5$ is methyl, and A is hydrogen or methyl These compounds may also be prepared by a process which comprises methylating a compound of formula (I) wherein X is CO, m is 0, $R_5$ is hydrogen and A is hydrogen with excess methylating agent under the appropriate conditions, and optionally carrying out the aforesaid X conversions.

Compounds wherein $R_5$ is methyl and A is hydrogen will be formed first — further excess of methylating agent will give the corresponding A = methyl compound.

4. Compounds of the formula (I) wherein m is 0, $R_5$ is methyl and A is $CO_2B$ The process comprises cyclising a compound of formula (XII):

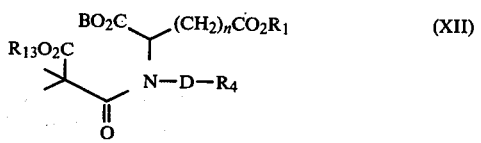

(XII)

wherein $CO_2R_{13}$ is an ester group, to give a compound of the formula (I) wherein X is CO, and thereafter if desired carrying out the aforesaid X conversion reactions.

Most suitably $R_{13}$ is a $C_{1-4}$ alkyl group or a benzyl group or the like, and the groups $R_{13}$, B and $R_1$ are the same $C_{1-4}$ alkyl group such as the methyl or ethyl groups. Generally, the cyclisation reaction takes place in a dry organic solvent using a strong base such as sodium hydride or sodium ethoxide (or other $-OR_{13}$ or $-OB$ group) to bring about the initial proton abstraction from the methine group. It has been found that sodium ethoxide in benzene or potassium t-butoxide in toluene, benzene or hexamethylphosphoramide give good results.

5. Compounds of the formula (I) wherein $R_5$ and A are hydrogen

The process comprises decarboxylating a compound of formula (XIII):

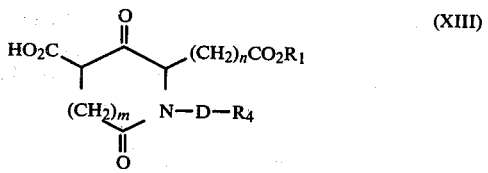

(XIII)

and thereafter if desired converting X from CO to other values in the aforesaid manner.

The decarboxylation reaction may be brought about under basic, acid or neutral conditions in conventional manner. For example when m = 0 the reaction is conveniently effected by heating the chosen compound of the formula (XIII) in a suitable solvent such as toluene or xylene.

It is frequently convenient however to generate the desired compound of the formula (I) directly from an ester of the formula (XIV), and often this will in fact be the preferred route:

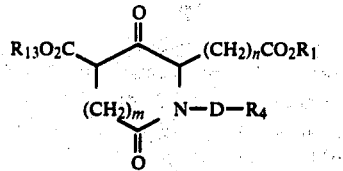

(XIV)

It has been found that often it is sufficient to bring about de-esterification and subsequent decarboxylation in the chosen compound of the formula (XIV) simply to leave the compound standing in an inert solvent, for example overnight. Otherwise the desired de-esterification and decarboxylation in the chosen compound of the formula (XIV) can be brought about by treatment with, for example, lithium iodide dihydrate in anhydrous solvents. In cases where m = 0, the compound of the formula (XIV) can also for example be de-esterified and decarboxylated by heating the compound alone or preferably in a high boiling solvent such as toluene or xylene.

After these Processes 1 to 5, $R_1$ may be varied by conventional de-esterification and/or esterification reactions. Similarly protected CROH and $R_3$ hydroxy moieties may be deprotected by conventional methods. For example, when $R_3$ is a benzyloxy group, the benzyl group may readily be removed by hydrogenolysis. Thus it may be seen that 'protected hydroxy' compounds of the formula (I) are useful intermediates in the preparation of the corresponding 'free hydroxy' compounds of the formula (I).

The conversion of a compound of the formula (I) wherein X is CO to the corresponding compound wherein X is protected CO may be carried out under conventional reaction conditions for, for example, carbonyl addition and condensation reactions.

The conversion of a compound of the formula (I) wherein X is CO to the corresponding compound wherein X is CHOH may be carried out by conventional methods for reducing a ketone to an alcohol, for example by sodium borohydride reduction.

The conversion of a compound of the formula (I) wherein X is CO to the corresponding compound wherein X is CROH in which R is $C_{1-4}$ alkyl may be carried out by conventional Grignard or alkyl metal, (suitably alkyl lithium) reactions.

When $R_1$ is hydrogen, salts of compounds of the formula (I) may be prepared in conventional manner, for example, by reacting the chosen compound of the formula (I) with the required base.

Intermediates for Process 1 to 5

Process 1

Compounds of formula (XI) wherein A is $CO_2B$ may be prepared by the cyclisation of a compound of formula (XV):

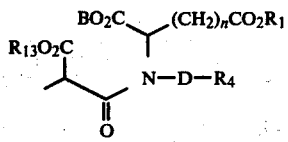

(XV)

Often in this cyclisation reaction a mixture of products will be obtained, and the required compound of the formula (XI) wherein A is $CO_2B$ will be separated therefrom by conventional methods.

The reaction is carried out as for the cyclisation described in Process 4.

The compounds of the formula (XV) may be prepared by an exactly analogous method to that used for the preparation of compounds of formula (XII) as described below.

When A is hydrogen in the compound of the formula (XI) then this compound of the formula (XI) may be prepared by the monomethylation of a compound of formula (XVI):

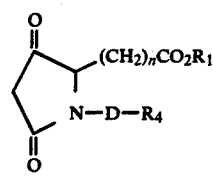

(XVI)

This monomethylation will be carried out by conventional methods such as those described in Process 1 for the monomethylation of a compound of the formula (XI). After the monomethylation it will often be necessary to separate the desired monomethyl compound of the formula (XI) from byproducts formed in the reaction, and this may be done in conventional manner.

Process 4

The compounds of the formula (XII) may be prepared by the reaction of a compound of formula (XVII):

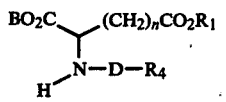

(XVII)

with a reactive acylating derivative of an acid of formula $HO_2C — C(CH_3)_2 — CO_2H$ or an ester thereof.

Suitable reactive acylating derivatives of this acid include $R_{13}O_2C — C(CH_3)_2 — CO — Z$ wherein Z is a readily displaceable group such as Cl, Br, $OSO_2CH_3$, $OSO_2C_6H_4CH_3$ or the like; or such derivatives wherein Z is OH in the presence of dicyclohexyl carbodiimide as a condensing agent.

The compounds (XVII) may be prepared by the reaction of an amine (XVIII):

$$H_2N — D — R_4 \quad\quad (XVIII)$$

with a compound of formula (XIX):

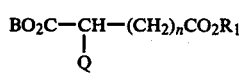

(XIX)

wherein Q is a group readily displaceable by an electron rich group.

The displacement reaction occurs under conventional reaction conditions, for example, in an alcoholic solvent in the presence of $Na_2CO_3$ or pyridine.

The preparation of the required amine of formula (XVIII) will be a routine matter to the skilled chemist. Two suitable preparations are illustrated in the Examples.

Process 5

Compounds of the formula (XIV) may be prepared by the cyclisation of a compound of formula (XX):

$$R_{13}O_2C \underset{(CH_2)_m}{\overset{BO_2C}{\diagup}} \underset{\underset{O}{\overset{\|}{N-D-R_4}}}{\diagdown} (CH_2)_nCO_2R_1 \qquad (XX)$$

in the usual manner.

These compounds (XX) may be prepared in an exactly analogous manner to the preparation described above for compounds of the formula (XII).

The intermediates of formulae (XI) to (XX) are believed to be novel, and as such form important aspects of the present invention.

Compounds within the formula (I) have useful pharmacological activity. For example compounds within the formula (I) have anti-gastric secretion activity, anti-ulcer activity, cardiovascular activity e.g. anti-hypertensive activity, platelet aggregration inhibition activity, affect the respiratory tract e.g. bronchodilator activity, and have anti-fertility and smooth muscle activity.

In general it may be said that compounds within the formula (I) have a range of pharmacological activities similar to those shown by the natural prostaglandins, but that these activities tend to be rather more selective. They have also proved to be beneficially stable compounds, particularly compounds wherein $R_5$ is methyl.

The invention therefore also provides a pharmaceutical composition comprising a compound of the formula (I) and a pharmaceutically acceptable carrier.

Clearly the formulation of the said pharmaceutical composition will depend on the nature of the activity shown by the chosen compound of the formula (I), and on other factors such as a preference in a particular area of therapy for a particular mode of administration.

The compositions may be in the form of tablets, capsules, powders, granules, lozenges or liquid preparations, such as oral or sterile parenteral solutions or suspensions.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents, and the like.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

When appropriate, the compositions of this invention may be presented as an aerosol for oral administration, or as a microfine powder for insufflation.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention also provides a method of treatment and/or prophylaxis of disorders in human beings which comprises the administration to the sufferer of an effective amount of a compound of the formula (I).

The following Examples illustrate the preparation of compounds of the formula (I) and their pharmacological properties.

EXAMPLE 1

$$(PhCH_2)_2 \overset{O}{\overset{\|}{N}} CCH_2CH_2 \overset{O}{\overset{\|}{C}} CH_3$$

N,N-Dibenzyl-4-oxo-valeramide

A solution of levulinic acid (58 g) in dry methylene chloride (300 ml) was added to a solution of dibenzylamine (98.5 g) in dry methylene chloride (300 ml). The mixture was stirred at 0° and a solution of dicyclohexylcarbodiimide (106 g) in dry methylene chloride (300 ml) was added dropwise. Stirring was continued for 3 hours.

The mixture was filtered and the filtrate evaporated in vacuo. The residue was taken up in ether and filtered. The filtrate was washed with dilute hydrochloric acid, sodium bicarbonate solution and then with sodium chloride solution until the washings were neutral. The ether layer was dried over anhydrous sodium sulphate and evaporated in vacuo to give N,N-dibenzyl-4-oxo-valeramide as a yellow oil (120 g).

| I.R. spectrum | - amide carbonyl absorption at 1640 cm$^{-1}$.<br>- carbonyl absorption at 1705 cm$^{-1}$. |
|---|---|
| N.M.R. spectrum | - 10 proton singlet at 2.85 $\tau[(C_6H_5CH_2)_2N-]$<br>- 4 proton singlet at 5.55 $\tau[(PhCH_2)_2N-]$<br>- 4 proton broad multiplet at 7.4 $\tau$ $(>N-\overset{O}{\overset{\|}{C}}CH_2CH_2-)$<br>- 3 proton singlet at 7.9$\tau[-\overset{O}{\overset{\|}{C}}-CH_3]$ |

The compounds shown in Table 1 were similarly prepared

Table 1

$$(PhCH_2)_2N\overset{O}{\overset{\|}{C}}(CH_2)_n\overset{O}{\overset{\|}{C}}CH_3$$

| Compound | n | Carbonyl absorptions cm$^{-1}$ | |
|---|---|---|---|
| 1 | 3 | 1705, | 1640 |

Table 1-continued

| Compound | n | Carbonyl absorptions cm$^{-1}$ | |
|---|---|---|---|
| 2 | 4 | 1705, | 1640 |

EXAMPLE 2

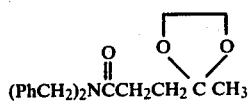

N,N-Dibenzyl-4-(1,3-dioxolano)-valeramide

Ethanediol (50 g) and toluene p-sulphonic acid (1 g) were added to a solution of N,N-dibenzyl-4-oxo-valeramide (120 g) in dry benzene (600 ml) and the mixture was refluxed under a Dean and Stark head for 3 hours.

The reaction mixture was allowed to cool and was then washed with sodium carbonate solution and with water until the washings were neutral, dried over anhydrous sodium sulphate and evaporated in vacuo to give N,N-dibenzyl-4-(1,3-dioxolano)-valeramide as a yellow oil (115 g).

| I.R. spectrum | - amide carbonyl absorption at 1640 cm$^{-1}$.<br>- absence of ketone carbonyl absorption. |
|---|---|
| N.M.R. spectrum | - 10 proton singlet at 2.85τ[(C$_6$H$_5$CH$_2$)$_2$N—]<br>- 4 proton singlet at 5.55τ[(PhCH$_2$)$_2$N—] |

- 4 proton singlet at 6.2τ 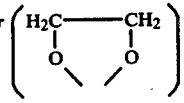

- 4 proton broad multiplet at 7.8τ

$$(\text{>N—CCH}_2\text{CH}_2\text{—})$$

- 3 proton singlet at 8.8τ

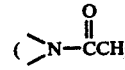

The compounds shown in Table 2 were similarly prepared

Table 2

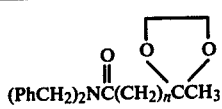

| Compound | n | Carbonyl absorption (cm$^{-1}$) |
|---|---|---|
| 3 | 3 | 1705 |
| 4 | 4 | 1705 |

EXAMPLE 3

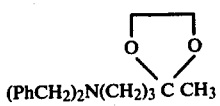

N,N-Dibenzyl-5-amino-pentan-2-one ethylene acetal

N,N,-Dibenzyl-4-(1,3-dioxolano)-valeramide (115 g) in dry tetrahydrofuran (300 ml) was added dropwise to a suspension of lithium aluminium hydride (17 g) in dry tetrahydrofuran (500 ml). The mixture was gently refluxed for 2 hours.

The mixture was cooled in an ice-bath and water (300 ml) was added dropwise. The reaction mixture was stirred at room temperature for 30 minutes and filtered. The residue was washed several times with ether and the combined organic fractions were washed with water and dried over anhydrous sodium sulphate and evaporated in vacuo to give N,N-dibenzyl-5-amino-pentan-2-one ethylene acetal as a yellow oil (90 g).

| I.R. spectrum | - absence of amide carbonyl absorption. |
|---|---|
| N.M.R. spectrum | - 10 proton singlet at 2.8τ[C$_6$H$_5$CH$_2$)$_2$N—] |

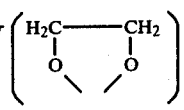

- 4 proton singlet at 6.5τ[(PhCH$_2$)$_2$N—]
- 2 proton broad multiplet at 7.65 τ(N—CH$_2$—)
- 4 proton broad multiplet at 8.5τ

- 3 proton singlet at 8.85τ

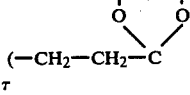

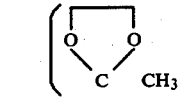

The compounds shown in Table 3 were similarly prepared

Table 3

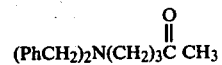

| Compound | n |
|---|---|
| 5 | 4 |
| 6 | 5 |

EXAMPLE 4

$$(\text{PhCH}_2)_2\text{N(CH}_2)_3\overset{\text{O}}{\overset{\|}{\text{C}}}\text{CH}_3$$

N,N,-Dibenzyl-3-aminopropyl methyl ketone

A solution of N,N-dibenzyl-5-amino-pentan-2-one ethylene acetal (90 g) in ethanol (500 ml) containing dilute hydrochloric acid (200 ml) was refluxed for 1 hour. The solution was allowed to cool and the ethanol was evaporated in vacuo. The residue was dissolved in water and extracted with ether. The aqueous layer was made alkaline with dilute sodium hydroxide solution and was extracted twice with ether. The combined ethereal extracts were washed with water, dried over anhydrous sodium sulphate and evaporated in vacuo, to give a brown oil. The product was purified by chromatography to give N,N-dibenzyl-3-aminopropylmethyl ketone as a red-brown oil (60 g).

| I.R. spectrum | - carbonyl absorption at 1700 cm$^{-1}$ |
|---|---|
| N.M.R.spectrum | - 10 proton singlet at 2.7τ[(C$_6$H$_5$CH$_2$)$_2$N—] |
| | - 4 proton singlet at 6.5τ[(PhCH$_2$)$_2$N—] |
| | - 4 proton broad multiplet at 7.6τ |
| | $(NCH_2-\overset{\overset{O}{\|}}{C}-CH_2-\overset{\overset{O}{\|}}{C}-)$ |
| | - 3 proton singlet at 8.0τ(—C—CH$_3$) |
| | - 2 proton broad multiplet at 8.3τ |
| | $(-H_2C-CH_2-CH_2-\overset{\overset{O}{\|}}{C})$ |

The compounds shown in Table 4 were similarly prepared

Table 4

$$(PhCH_2)_2N(CH_2)_n\overset{\overset{O}{\|}}{C}CH_3$$

| Compound | n | Carbonyl absorption (cm$^{-1}$) |
|---|---|---|
| 7 | 4 | 1700 |
| 8 | 5 | 1700 |

EXAMPLE 5

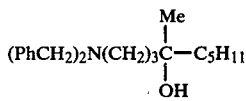

(PhCH$_2$)$_2$N(CH$_2$)$_3$C—C$_5$H$_{11}$ with Me above and OH below

4-Methyl-1-(N,N-dibenzylamino)-nonan-4-ol

Pentyl magnesium bromide was prepared under nitrogen from magnesium (8 g) and pentyl bromide (50.3 g) in dry tetrahydrofuran (150 ml).

A solution of N,N,-dibenzyl-3-aminopropyl methyl ketone (45 g) in dry tetrahydrofuran (200 ml) was added dropwise to the Grignard reagent. The mixture was stirred and refluxed overnight.

A saturated solution of ammonium chloride was added and the product extracted three times with ether. The organic fractions were combined, washed with sodium chloride solution, dried over anhydrous sodium sulphate and evaporated in vacuo to give 4-methyl-1-(N,N-dibenzylamino)nonan-4-ol as a brown oil (60 g).

| I.R. spectrum | - broad OH absorption at 3300 cm$^{-1}$. |
|---|---|
| | - absence of carbonyl absorption. |

The compounds shown in Table 5 were similarly prepared.

Table 5

(PhCH$_2$)$_2$N(CH$_2$)$_n$CR$_4$ with HO and CH$_3$ branches

| Compound | Grignard Reagent | n | R$_4$ | OH absorption cm$^{-1}$ |
|---|---|---|---|---|
| 9 | C$_4$H$_9$MgBr | 4 | C$_4$H$_9$ | 3300 |
| 10 | PhCH$_2$CH$_2$MgBr | 3 | CH$_2$CH$_2$Ph | 3300 |
| 11 | C$_3$H$_7$MgBr | 5 | C$_3$H$_7$ | 3300 |

EXAMPLE 6

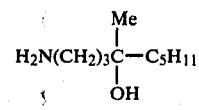

H$_2$N(CH$_2$)$_3$C—C$_5$H$_{11}$ with Me above and OH below

1-Amino-4-methyl-nonan-4-ol

A solution of 4-methyl-1-(N,N-dibenzylamino)-nonan-4-ol (50 g) in ethanol (200 ml) was added to a slurry of 10% Pd/C (6 g) in ethanol. One drop of concentrated hydrochloric acid was then added to the mixture.

The mixture was hydrogenated at 70° and 200 p.s.i. for 3 days. The mixture was filtered through kieselguhr and evaporated. The oily product was fractionally distilled to give 1-amino-4-methyl-nonan-4-ol as a colourless liquid (7 g), b.p. 110°–115°/0.5 mm Hg.

I.R. spectrum — broad absorption at 3300 cm$^{-1}$ due to OH,NH$_2$

N.M.R. spectrum — 3 proton singlet at 7.8 τ which disappears on shaking with D$_2$O.

The compounds shown in Table 6 were similarly prepared.

Table 6

H$_2$N(CH$_2$)$_n$CR$_4$ with HO and Me branches

| Compound | n | R$_4$ | NH$_2$,OH absorption cm$^{-1}$ |
|---|---|---|---|
| 12 | 4 | C$_4$H$_9$ | 3300 |
| 13 | 3 | CH$_2$CH$_2$Ph | 3300 |
| 14 | 5 | C$_3$H$_7$ | 3300 |

EXAMPLE 7

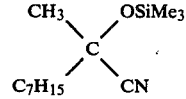

CH$_3$ and OSiMe$_3$ on C, with C$_7$H$_{15}$ and CN

2-Methyl-2-trimethylsilyloxy nonanitrile

Trimethylsilylcyanide (17.4 g) was slowly added to a stirred solution of 2-nonanone (24.9 g) and zinc iodide (1.12 g). The reaction mixture was cooled by periodic use of an ice — salt bath during the addition. The mixture was then stirred for 1 hour at room temperature.

| I.R. spectrum | - 1250, 850, 760 cm$^{-1}$ (—Si—CH$_3$) |
|---|---|
| N.M.R. spectrum | - 9 proton singlet at 9.75τ (—OSi(CH$_3$)$_3$) |

EXAMPLE 8

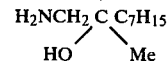

H$_2$NCH$_2$ C C$_7$H$_{15}$ with HO and Me branches

2-Hydroxy-2-methyl-n-nonylamine

2-Methyl-2-trimethylsilyloxy-n-nonanitrile (42.3 g) in dry ether (100 ml) was added dropwise to a stirred suspension of lithium aluminium hydride (13.4 g) in dry ether (350 ml). Reflux occurred and this was maintained by external heating for 1 hour after the final addition. The mixture was cooled to 0° and water (13.5 ml), 15% sodium hydroxide solution (13.5 ml) and water (40 ml) were added dropwise in sequence. The resulting mixture was stirred for half-an-hour at room temperature, then was filtered through Kieselguhr. The resulting solution was dried over sodium sulphate and evaporated in vacuo to give 2-hydroxy-2-methyl-n-nonylamine, b.p. 97°–99°/0.25 mm Hg.

EXAMPLE 9

$$EtO_2C-CH(CH_2)_6CO_2Et$$
$$|$$
$$HN-(CH_2)_3-C(C_5H_{11})(Me)$$
$$HO$$

Diethyl 2-(N-4′-hydroxy-4′-methyl-n-nonyl)-aminoazelate

A solution of diethyl-2-bromoazelate (13.1 g) in dry ethanol (50 ml) was added dropwise to a refluxing solution of 1-amino-4-methyl-nonan-4-ol (6.9 g) in dry ethanol (75 ml) containing a suspension of anhydrous sodium carbonate (6 g). The mixture was refluxed with stirring for 12 hours.

The reaction mixture was filtered and the filtrate evaporated in vacuo. The residue was taken up in ether (150 ml) and the ethereal solution was washed with sodium chloride solution until the washings were neutral, dried over anhydrous sodium sulphate and evaporated in vacuo to give diethyl 2-(N-4′-hydroxy-4′-methyl-n-nonyl)-aminoazelate as a yellow oil (15.8 g).

I.R. spectrum — ester carbonyl absorption at 1720 $cm^{-1}$.

The compounds shown in Table 7 were similarly prepared.

Table 7

$$R_1O_2C-CH(CH_2)_6CO_2R_1$$
$$|$$
$$HN-(CH_2)_nCR_4$$
$$HO\ Me$$

| Compound | n | $R_1$ | $R_4$ |
|---|---|---|---|
| 15 | 4 | Me | $C_4H_9$ |
| 16 | 3 | Me | $CH_2CH_2Ph$ |
| 17 | 3 | Me | $C_5H_{11}$ |
| 18 | 1 | Me | $C_7H_{15}$ |
| 19 | 5 | Me | $C_3H_7$ |

EXAMPLE 10

$$EtO_2C-CH(CH_2)_6CO_2Et$$
$$EtO_2C-CH_2-C(=O)-N-(CH_2)_3C(C_5H_{11})(Me)(OH)$$

Diethyl 2-[N-(4′-hydroxy-4′-methyl-n-nonyl)-N-ethoxycarbonylacetyl]-aminoazelate A solution of monoethyl malonate (0.6 g) in dry methylene chloride (15 ml) was added to a solution of diethyl 2-(N-4′-hydroxy-4′-methyl-n-nonyl)-aminoazelate (2.075 g) in dry methylene chloride (15 ml). The mixture was stirred at room temperature and a solution of dicyclohexylcarbodiimide (1.03 g) in dry methylene chloride (15 ml) was added dropwise. Stirring was continued for 3 hours.

The mixture was filtered and the filtrate evaporated in vacuo. The residue was taken up in ether and filtered. The ethereal solution was washed with dilute hydrochloric acid, sodium bicarbonate solution and then with sodium chloride solution until the washings were neutral. The ether layer was dried over anhydrous sodium sulphate and evaporated in vacuo to give diethyl 2-[N-(4′-hydroxy-4′-methyl-n-nonyl)-N-ethoxycarbonylacetyl]-aminoazelate as a yellow oil, (2.3 g).

I.R. spectrum - ester carbonyl absorption at 1730 $cm^{-1}$.
- amide carbonyl absorption at 1650 $cm^{-1}$.

The compounds shown in Table 8 were similarly prepared.

Table 8

$$R_1O_2C-C(CH_2)_6CO_2R_1$$
$$EtO_2C-CH_2-C(=O)-N-(CH_2)_nCR_4$$
$$HO\ Me$$

I.R. SPECTRUM

| Compound | n | $R_1$ | $R_4$ | OH absorption ($cm^{-1}$) | Amide carbonyl absorption ($cm^{-1}$) |
|---|---|---|---|---|---|
| 20 | 4 | Me | $C_4H_9$ | 3400 | 1640 |
| 21 | 3 | Me | $CH_2CH_2Ph$ | 3400 | 1640 |
| 22 | 3 | Me | $C_5H_{11}$ | 3400 | 1650 |
| 23 | 1 | Me | $C_7H_{15}$ | 3400 | 1650 |
| 24 | 5 | Me | $C_3H_7$ | 3400 | 1640 |

EXAMPLE 11

$$EtO_2C-[pyrrolidine-3,5-dione with (CH_2)_6CO_2Et and N-(CH_2)_3C(C_5H_{11})(Me)(OH)]$$

4-Ethoxycarbonyl-2-(6′-ethoxycarbonyl-n-hexyl)-1-(4″-hydroxy-4″-methyl-n-nonyl)-pyrrolidin-3,5-dione Potassium tert-butoxide (0.54 g) was added in small portions over 30 minutes to a warm solution of diethyl 2-[N-(4′-hydroxy-4′methyl-n-nonyl)-N-ethoxycarbonylacetyl]-aminoazelate (2.3 g) in dry toluene (100 ml). The mixture was gently refluxed for 1½ hours.

The solvent was evaporated in vacuo and the residue was taken up in water. The solution was extracted twice with ether and the aqueous layer was acidified with dilute hydrochloric acid and extracted with ether. This ethereal solution was washed with sodium chloride solution and dried over anhydrous sodium sulphate to give a solution of 4-ethoxycarbonyl-2-(6′-ethoxycarbonyl-n-hexyl)-1-(4″-hydroxy-4″-methyl-n-nonyl)-pyrrolidin-3,5-dione.

The compounds shown in Table 9 were similarly prepared.

Table 9

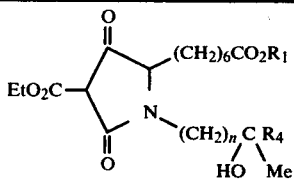

| Compound | n | $R_1$ | $R_4$ |
|---|---|---|---|
| 25 | 4 | Me | $C_4H_9$ |
| 26 | 3 | Me | $CH_2CH_2Ph$ |
| 27 | 3 | Me | $C_5H_{11}$ |
| 28 | 1 | Me | $C_7H_{15}$ |
| 29 | 5 | Me | $C_3H_7$ |

EXAMPLE 12

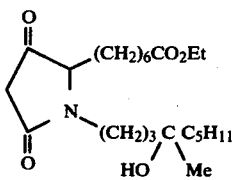

2-(6'-Ethoxycarbonyl-n-hexyl)-1-(4''-hydroxy-4''-methyl-n-nonyl)-pyrrolidin-3,5-dione.

A solution of 4-ethoxycarbonyl-2-(6'-ethoxycarbonyl-n-hexyl)-1-(4''-hydroxy-4''-methyl-n-nonyl)-pyrrolidin-3,5-dione in ether was allowed to stand over anhydrous sodium sulphate overnight. The solution was filtered and the filtrate evaporated to give an orange oil. The product was purified by chromatography to give 2-(6'-ethoxycarbonyl-n-hexyl)-1-(4''-hydroxy-4''-methyl-n-nonyl)-pyrrolidin-3,5-dione as a pale yellow oil.

I.R. spectrum - broad OH absorption at 3500 cm$^{-1}$.
- amide carbonyl absorption at 1685 cm$^{-1}$.
- ester carbonyl absorption at 1730 cm$^{-1}$.
- carbonyl absorption at 1770 cm$^{-1}$.

The compounds shown in Table 10 were similarly prepared.

Table 10

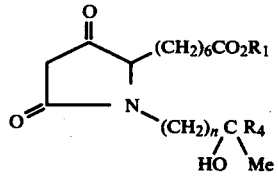

| | | | | I.R. SPECTRUM | |
|---|---|---|---|---|---|
| Compound | n | $R_1$ | $R_4$ | OH absorption (cm$^{-1}$) | Carbonyl absorptions (cm$^{-1}$) |
| 30 | 4 | Me | $C_4H_9$ | 3400 | 1760, 1730, 1690 |
| 31 | 3 | Me | $CH_2CH_2Ph$ | 3400 | 1760, 1730, 1685 |
| 32 | 3 | Me | $C_5H_{11}$ | 3400 | 1770, 1730, 1685 |
| 33 | 1 | Me | $C_7H_{15}$ | 3400 | 1760, 1730, 1680 |
| 34 | 5 | Me | $C_3H_7$ | 3400 | 1760, 1730, 1685 |

EXAMPLE 13

2-(6'-Methoxycarbonyl-n-hexyl)-3-hydroxy-1-(4''-hydroxy-4''-methyl-n-nonyl)-pyrrolidin-5-one Sodium borohydride (290 mg) was added in portions to a stirred solution of 2-(6'-methoxycarbonyl-n-hexyl)-1-(4''-hydroxy-4''-methyl-n-nonyl)-pyrrolidin-3,5-dione (2.5 g) in dry methanol (30 ml). Stirring was continued for 2 hours at room temperature.

The solvent was evaporated in vacuo and the residue was dissolved in ether. The ethereal solution was washed with very dilute hydrochloric acid and with water, dried over sodium sulphate and evaporated in vacuo to give a yellow gum.

The product was purified by chromatography to give 2-(6'-methoxy-carbonyl-n-hexyl)-3-hydroxy-1-(4''-hydroxy-4''-methyl-n-nonyl)-pyrrolidin-5-one as a pale yellow gum (900 mg).

I.R. spectrum - broad OH absorption 3400 cm$^{-1}$
- carbonyl absorptions 1730, 1660 cm$^{-1}$ The compounds shown in Table 11 were similarly prepared.

Table 11

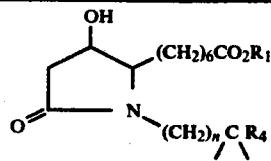

| | | | | I. R. SPECTRUM | |
|---|---|---|---|---|---|
| Compound | n | $R_1$ | $R_4$ | OH absorption (cm$^{-1}$) | Carbonyl absorptions (cm$^{-1}$) |
| 35 | 4 | Me | $C_4H_9$ | 3400 | 1730, 1670 |
| 36 | 3 | Me | $CH_2CH_2Ph$ | 3400 | 1720, 1660 |
| 37 | 1 | Me | $C_7H_{15}$ | 3400 | 1730, 1670 |

| | MASS SPECTRUM | |
|---|---|---|
| Compound | Molecular ion | Base peak |
| 35 | — | 342 M$^+$ - $C_4H_9$ |
| 36 | 433 | 328 M$^+$ - $CH_2CH_2Ph$ |

EXAMPLE 14

2-(6'-Carboxy-n-hexyl)-3-hydroxy-1-(2''-hydroxy-2''-methyl-n-nonyl)-pyrrolidin-5-one thanol (20 ml). The mixture was gently refluxed for 24 hours.

The solvent was evaporated in vacuo and the residue was taken up in water. The aqueous solution was extracted with ether and acidified with dilute hydrochloric acid. The acid solution was extracted with ether and this ethereal solution was washed with water, dried over magnesium sulphate and evaporated in vacuo to give 2-(6'-carboxy-n-hexyl)-3-hydroxy-1-(2''-hydroxy-2''-methyl-n-nonyl)-pyrrolidin-5-one as a yellow gum (400 mg).

I.R. Spectrum - broad OH absorption around 3450 cm$^{-1}$
carbonyl absorptions at 1710, 1670 cm$^{-1}$
Mass Spectrum - Base peak 367 M$^+$—H$_2$O

EXAMPLE 15

4,4-Dimethyl-2-(6'-ethoxycarbonyl-n-hexyl)-1-(4''-hydroxy-4''-methyl-n-nonyl)-pyrrolidin-3,5-dione Sodium hydride (0.87 g, 80% dispersion in mineral oil) was washed with hexane, blown dry under nitrogen and suspended in dry benzene (25 ml). A solution of 2-(6'-ethoxycarbonyl-n-hexyl)-1-(4''-hydroxy-4''-methyl-n-nonyl)-pyrrolidin-3,5-dione (3 g) in dry benzene (30 ml) was added and the mixture was stirred at room temperature under nitrogen for 1 hour.

The mixture was heated to 70° and a solution of methyl iodide (10 g) in dry benzene (10 ml) was added dropwise. The mixture was heated at 70° for 2 hours.

The reaction mixture was cooled and glacial acetic acid (1 ml) was added. The mixture was filtered and the filtrate evaporated in vacuo to give a yellow oil. The product was purified by column chromatography to give 4,4-dimethyl-2-(6'-ethoxycarbonyl-n-hexyl)-1-(4''-hydroxy-4''-methyl-n-nonyl)-pyrrolidin-3,5-dione as a yellow oil (1.0 g).

I.R. spectrum - carbonyl absorptions at 1760, 1730 and 1690 $cm^{-1}$
- broad OH absorption at 3450 $cm^{-1}$.

The compounds shown in Table 12 were similarly prepared

Table 12

[Structure: pyrrolidin-3,5-dione with (CH$_2$)$_6$CO$_2$R$_1$ substituent and N-(CH$_2$)$_n$CR$^4$(OH)(Me) substituent]

| Compound | n | R$_1$ | R$_4$ | OH absorption $cm^{-1}$ | Carbonyl absorption $cm^{-1}$ |
|---|---|---|---|---|---|
| 38 | 4 | Me | C$_4$H$_9$ | 3450 | 1760, 1730, 1690 |
| 39 | 3 | Me | CH$_2$CH$_2$Ph | 3450 | 1760, 1730, 1685 |
| 40 | 3 | Me | C$_5$H$_{11}$ | 3450 | 1760, 1730, 1680 |
| 41 | 1 | Me | C$_7$H$_{15}$ | 3450 | 1760, 1730, 1685 |

EXAMPLE 16

1-(4'-Hydroxy-4'-methyl-n-nonyl)-2-(6''-methoxycarbonyl-n-hexyl)-2,4,4-trimethyl-pyrrolidin-3,5-dione A solution of 1-(4'-hydroxy-4'-methyl-n-nonyl)-2-(6''-methoxycarbonyl-n-hexyl)-pyrrolidin-3,5-dione (4 g) in dry dimethylformamide (25 ml) was slowly added to a suspension of sodium hydride (1.3 g, 80% dispersion in mineral oil) in dry benzene (20 ml) and dry dimethylformamide (20 ml). The mixture was stirred for 2 hours under nitrogen at room temperature.

A solution of methyl iodide (15 g) in dry dimethylformamide (10 ml) was added dropwise and stirring was continued for 3 hours.

Glacial acetic acid (1 ml) was added and the solvent was removed in vacuo. The residue was taken up in ether and the ethereal solution was washed with water, dried over magnesium sulphate and evaporated to give a yellow oil. The product was purified by column chromatography to give 1-(4'-hydroxy-4'-methyl-n-nonyl)-2-(6''-methoxycarbonyl-n-hexyl)-2,4,4-trimethyl-pyrrolidin-3,5-dione as a yellow oil (1.4 g).

I.R. spectrum - carbonyl absorptions at 1750, 1730, 1670 $cm^{-1}$
broad OH absorption at 3450 $cm^{-1}$.

EXAMPLE 17

2-(6'-carboxy-n-hexyl)-4,4-dimethyl-1-(5''-hydroxy-5''-methyl-n-nonyl)-pyrrolidin-3,5-dione A 10% solution of potassium carbonate (10 ml) was added to a solution of 4,4-dimethyl-2-(6'-methoxycarbonyl-n-hexyl)-1-(3''-hydroxy-3''-methyl-n-nonyl)-pyrrolidin-3,5-dione (600 mg) in ethanol (40 ml). The mixture was gently refluxed for 24 hours.

The solvent was evaporated in vacuo and the residue was taken up in water. The aqueous solution was extracted with ether and acidified with dilute hydrochloric acid. The acid solution was extracted with ether and this ethereal solution was washed with water, dried over magnesium sulphate and evaporated in vacuo to give 2-(6'-carboxy-n-hexyl)-4,4-dimethyl-1-(5''-hydroxy-5''-methyl-n-nonyl)-pyrrolidin-3,5-dione as a yellow gum (400 mg).

I.R. spectrum - carbonyl absorptions at 1760, 1710, 1670 $cm^{-1}$
broad OH absorption around 3400 $cm^{-1}$
Mass spectrum - Base Peak 354 $M^+$—$C_4H_9$

Pharmacological Data Section

The compounds were examined for their ability to inhibit 5-hydroxytryptamine induced bronchoconstriction in the anaesthetised, artifically respired guinea pig (Konzett-Rossler preparation - ref: H. Konzett and R. Rossler, 1940, Arch. exp. Path. Pharmak., 195, 71). 2-(6'-Methoxycarbonyl-n-hexyl)-1-(5''-hydroxy-5''-methyl-n-nonyl)-pyrrolidin-3,5-dione (Compound 30 of Table 10) inhibited bronchoconstriction with an IC$_{50}$ of 12 µg/kg, intravenously.

The compounds were examined for their ability to inhibit pentagastrin-stimulated gastric acid secretion in the anaesthetised, perfused rat stomach preparation (Ghosh and Schild preparation - ref: M. N. Ghosh and H. O. Schild, 1958, Brit. J. Pharmacol, 13, 54) 2-(6'-Ethoxycarbonyl-n-hexyl)-1-(4''-hydroxy-4''-methyl-n-nonyl)-pyrrolidin-3,5-dione (Compound of Example 12) and 4,4-dimethyl-2-(6'-methoxycarbonyl-n-hexyl)-1-(4''-hydroxy-4''-methyl-n-nonyl)-pyrrolidin-3,5-dione (Compound 40 of Table 12) were active in this test at 0.5 and 5 mg/kg, i.v., respectively.

The compounds were also examined for their ability to inhibit gastric acid secretion in the pyloric ligated rate model (Shay rat preparation - ref: H. Shay et al, 1945, Gastroenterology, 5, 43). 2-(6'-Ethoxycarbonyl-n-hexyl)-1-(4''-hydroxy-4''-methyl-n-nonyl)-pyrrolidin-3,5-dione (Compound of Example 12); 4,4-dimethyl-2-(6'-methoxycarbonyl-n-hexyl)-1-(4''-hydroxy-4''-methyl-n-nonyl)-pyrrolidin-3,5-dione (Compound 40 of Table 12); and 1-(4'-hydroxy-4'-methyl-n-nonyl)-2-(6''-methoxycarbonyl-n-hexyl)-2,4,4-trimethyl-pyrrolidin-3,5-dione (Compound of Example 16) were active in this test at 100, 150 and 100 mg/kg, intraduodenally, respectively.

The compounds were also examined for their ability to inhibit indomethacin induced gastric ulceration in the rat and the Compound of Example 12 was active in this anti-ulcer test at 100 mg/kg, orally. This same compound was also active in inhibiting cold restraint induced ulceration at 150 mg/kg, orally.

Toxicity

No toxic effects were observed at the doses given.

What we claim is:

1. A compound selected from the group consisting of a pyrrolidone of the formula:

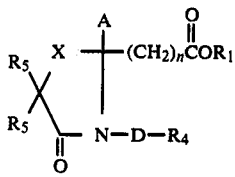

wherein n has a value of 4 to 8;

X is carbonyl; a ketal, thioketal, hemithioketal, oxime, semicarbazone or hydrazone derived from such carbonyl; or C(OH)R in which R is hydrogen or alkyl of 1 to 4 carbon atoms;

$R_1$ is hydrogen, alkyl of 1 to 12 carbon atoms, phenyl, benzyl or toluyl;

D is a hydroxyalkylene chain selected from the group consisting of

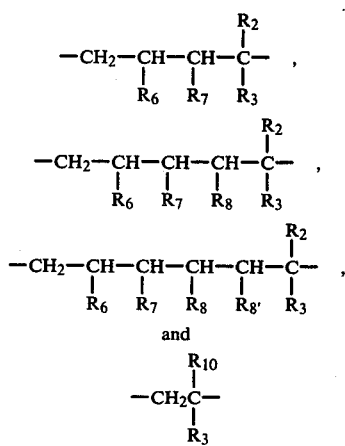

wherein $R_3$ is hydroxy, acyloxy of 1 to 4 carbon atoms, or benzyloxy and each of $R_2$, $R_6$, $R_7$, $R_8$, and $R_{10}$ is hydrogen, alkyl of 1 to 4 carbon atoms or phenyl;

$R_4$ is hydrogen, alkyl of 1 to 9 carbon atoms, cycloalkyl of 5 to 8 carbon atoms, phenyl, naphthyl, or alkyl of 1 to 6 carbon atoms substituted with cycloalkyl of 5 to 8 carbon atoms, phenyl or naphthyl, said phenyl and naphthyl being unsubstituted or substituted by up to three substituents selected from the group consisting of fluoro, chloro, bromo, trifluoromethyl, alkyl of 1 to 4 carbon atoms, nitro, and alkoxy of 1 to 4 carbon atoms; and each of A and $R_5$ is hydrogen or methyl, A being methyl only when $R_5$ is methyl, and the pharmaceutically acceptable non-toxic salts thereof.

2. A compound according to claim 1 wherein said pyrrolidone is of the formula:

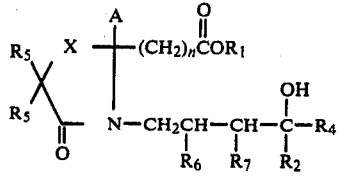

wherein n has a value of 5, 6 or 7;

X is carbonyl or hydroxymethylene;

$R_1$ is hydrogen or alkyl of 1 to 4 carbon atoms;

$R_2$ is methyl or ethyl;

each of $R_6$ and $R_7$ is hydrogen, methyl or ethyl;

$R_4$ is alkyl of 3 to 9 carbon atoms or phenethyl; and

A and $R_5$ are as therein defined.

3. A compound according to claim 2 wherein $R_4$ is alkyl of 3 to 9 carbon atoms.

4. A compound according to claim 2 wherein n is 6.

5. A compound according to claim 2 wherein $R_6$ and $R_7$ are hydrogen.

6. A compound according to claim 2 wherein
$R_2$ is methyl;
each of $R_6$ and $R_7$ is hydrogen and
each of A and $R_5$ is hydrogen.

7. A compound according to claim 2 wherein
$R_2$ is methyl;
each of $R_6$ and $R_7$ is hydrogen;
a is hydrogen; and
$R_5$ is methyl.

8. A compound according to claim 2 wherein
$R_2$ is methyl;
each of $R_6$ and $R_7$ is hydrogen; and
each of A and $R_5$ is methyl.

9. A compound according to claim 1 wherein said pyrrolidone is of the formula:

wherein n has a value of 5, 6 or 7;

X is carbonyl or hydroxymethylene;

$R_1$ is hydrogen or alkyl of 1 to 4 carbon atoms;

$R_2$ is methyl or ethyl;

each of $R_6$, $R_7$ and $R_8$ is hydrogen, methyl or ethyl;

$R_4$ is alkyl of 3 to 9 carbon atoms or phenethyl; and

A and $R_5$ are as therein defined.

10. A compound according to claim 9 wherein $R_4$ is alkyl of 3 to 9 carbon atoms.

11. A compound according to claim 9, wherein n is 6.

12. A compound according to claim 9 wherein $R_6$, $R_7$ and $R_8$ are hydrogen.

13. A compound according to claim 9 wherein
$R_2$ is methyl;
each of $R_6$, $R_7$ and $R_8$ is hydrogen; and
each of A and $R_5$ is hydrogen.

14. A compound according to claim 9 wherein
$R_2$ is methyl;
each of $R_6$, $R_7$ and $R_8$ is hydrogen;
A is hydrogen; and
$R_5$ is methyl.

15. A compound according to claim 9 wherein
$R_2$ is methyl;

each of $R_6$, $R_7$ and $R_8$ is hydrogen; and
each of A and $R_5$ is methyl.

16. A compound according to claim 1 wherein
n has a value of 5, 6 or 7;
X is carbonyl or hydroxymethylene;
$R_1$ is hydrogen or alkyl of 1 to 4 carbon atoms;
$R_4$ is alkyl of 3 to 9 carbon atoms;

D is 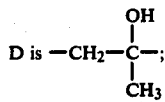

and

A and $R_5$ are as therein defined.

17. A compound according to claim 1 wherein said pyrrolidone is that compound depicted by the formula:

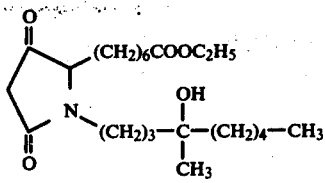

18. A compound according to claim 1 wherein said pyrrolidone is that compound depicted by the formula:

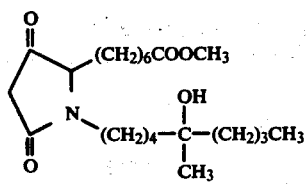

19. A compound according to claim 1 wherein said pyrrolidone is that compound depicted by the formula:

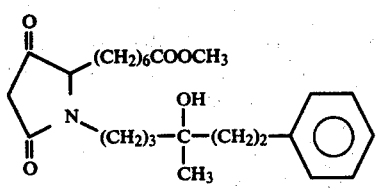

20. A compound according to claim 1 wherein said pyrrolidone is that compound depicted by the formula:

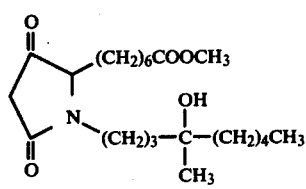

21. A compound according to claim 1 wherein said pyrrolidone is that compound depicted by the formula:

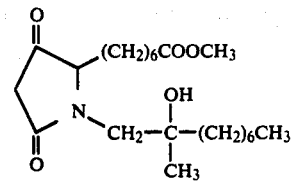

22. A compound according to claim 1 wherein said pyrrolidone is that compound depicted by the formula:

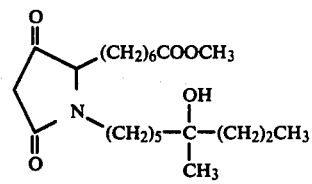

23. A compound according to claim 1 wherein said pyrrolidone is that compound depicted by the formula:

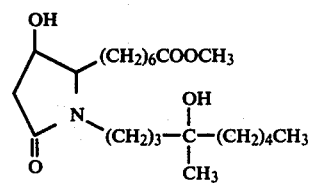

24. A compound according to claim 1 wherein said pyrrolidone is that compound depicted by the formula:

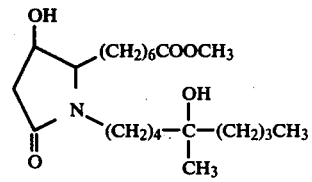

25. A compound according to claim 1 wherein said pyrrolidone is that compound depicted by the formula:

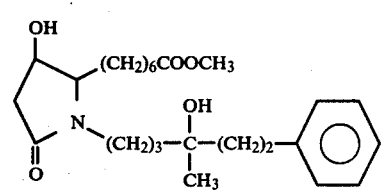

26. A compound according to claim 1 wherein said pyrrolidone is that compound depicted by the formula:

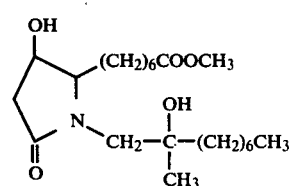

27. A compound according to claim 1 wherein said pyrrolidone is that compound depicted by the formula:

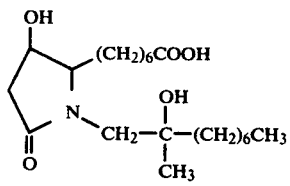

28. A compound according to claim 1 wherein said pyrrolidone is that compound depicted by the formula:

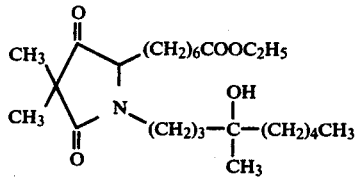

29. A compound according to claim 1 wherein said pyrrolidone is that compound depicted by the formula:

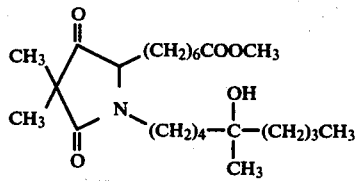

30. A compound according to claim 1 wherein said pyrrolidone is that compound depicted by the formula:

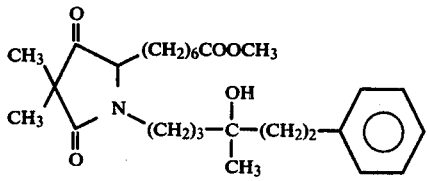

31. A compound according to claim 1 wherein said pyrrolidone is that compound depicted by the formula:

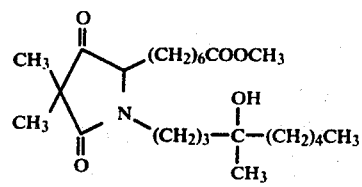

32. A compound according to claim 1 wherein said pyrrolidone is that compound depicted by the formula:

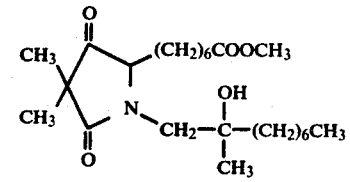

33. A compound according to claim 1 wherein said pyrrolidone is that compound depicted by the formula:

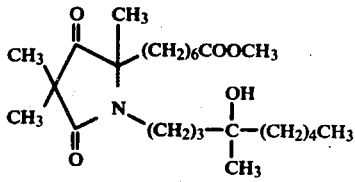

34. A compound according to claim 1 wherein said pyrrolidone is that compound depicted by the formula:

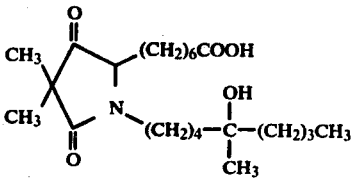

35. A pharmaceutical composition having natural prostaglandin-like properties comprising an effective amount of a compound according to claim 1 and a pharmaceutically acceptable carrier.

36. A method of treatment of prophylaxis of disorders susceptible to prostaglandin-like action which comprises the administration of an effective amount of a composition of claim 35.

37. A method of treatment or prophylaxis of disorders susceptible to prostaglandin-like action which comprises the administration of an effective amount of a compound according to claim 1.

* * * * *